US006440466B1

(12) United States Patent
Desai et al.

(10) Patent No.: US 6,440,466 B1
(45) Date of Patent: Aug. 27, 2002

(54) COMPOSITION FOR TREATING WHITE SPOT SYNDROME VIRUS (WSSV) INFECTED TIGER SHRIMP *PENAEUS MONODON* AND A PROCESS FOR PREPARATION THEREOF

(75) Inventors: Ulhas Manohar Desai; Chittur Thelakkat Achuthankutty; Rayadurga Anantha Sreepada, all of Goa (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/788,601

(22) Filed: Feb. 21, 2001

(51) Int. Cl.[7] ................................................ A61K 35/78
(52) U.S. Cl. ........................................ 424/725; 424/754
(58) Field of Search .............................. 424/754, 195.1, 424/725

(56) References Cited

U.S. PATENT DOCUMENTS 5,980,903 A  *  11/1999  Pruthi et al.
6,231,865 B1 *  5/2001   Hsu et al.
2001/0011544 A1 * 8/2001  Yamada et al.

FOREIGN PATENT DOCUMENTS

| JP | 62059214 | * | 3/1987 |
| WO | WO 009528945 | * | 11/1995 |

OTHER PUBLICATIONS

Tropilab Inc. (http://www.tropilab.com/medsupp.html, Mar. 27, 2000).*
Asia Source (wysiwyg://160/http://www.asiafood.org/glossary_1.cfm?alpha+B, 1998).*
Joseph (http://www.cis.um.edu.mt?~phcy/projects/final_year_projects/pcognocy.htm, 1994–1998).*

* cited by examiner

*Primary Examiner*—Christopher R. Tate
*Assistant Examiner*—Randall Winston
(74) *Attorney, Agent, or Firm*—Oliff & Berridge, PLC

(57) ABSTRACT

The present invention relates to a composition useful as prophylactic and/or therapeutic agent for the management of viral and bacterial diseases in aquatic animals, said composition containing effective amount of extract obtained from the plants *Lantena camera, Aegle marmelos, Ocimum sanctum, Mimosa pudica, Cynodon dactylon, Curcuma longa,* and *Allium sativum,* optionally in combination with a pharmaceutically acceptable carrier, diluents or excipients.

32 Claims, 10 Drawing Sheets

Figure 1:
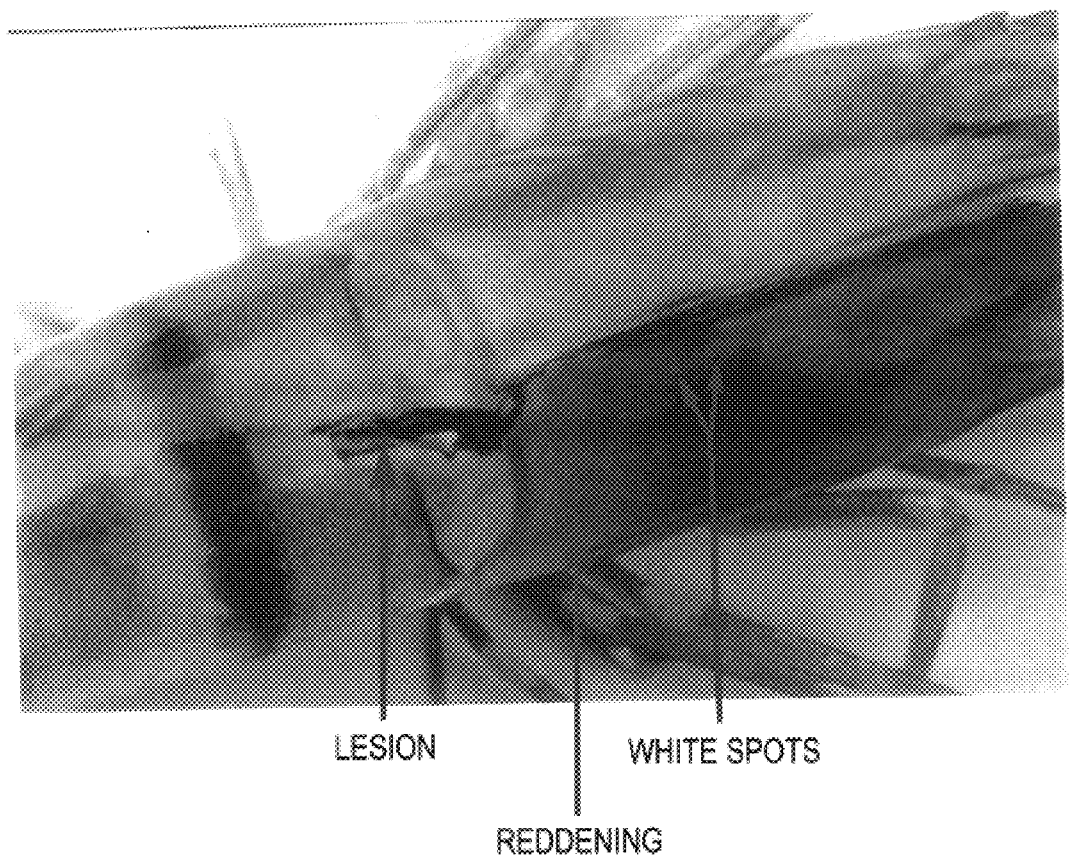

(5 of 10 Drawing Sheet(s) Filed in Color)

COMPOSITION FOR TREATING WHITE SPOT SYNDROME VIRUS (WSSV) INFECTED TIGER SHRIMP *PENAEUS MONODON* AND A PROCESS FOR PREPARATION THEREOF

FIELD OF THE INVENTION

The present invention relates to a composition useful as prophylactic and therapeutic agent for the management of viral diseases in aquatic animals, said composition containing aqueous extract of selected plants. The present invention also relates to a process for preparing the composition and a method of treating white spot syndrome virus (WSSV) infected tiger shrimp *Penaeus monodon*.

BACKGROUND AND PRIOR ART REFERENCES

In the tropics, particularly in Asian subcontinent, shrimp aquaculture has been growing as a major enterprise due to its export market and high profitability. In India, shrimp farming has transformed from a traditional farming practice into an organized industry in a short period of time. More than 100,000 hectares of coastal land are being used for shrimp farming in India, producing >80,000 tones annually (C. T. Achuthankutty, 1998. Sustainable shrimp farming in India—Prospects and challenges. In Technological Advancements in Fisheries, Edited by M. S. Hameed & B. M. Kurup, Publ. No.1, School Indl. Fish., Cochin University of Science and Technology, Cochin, p. 54–59). Different species of shrimps are being cultivated in different parts of the world, but the tiger shrimp, *Penaeus monodon* is the most favored species for farming in India.

Since 1992, the shrimp culture industry, particularly in Asia, has been threatened by a viral syndrome, commonly known as the 'white spot disease', causing heavy mortality and financial losses (Y. G. Wang; M. Shariff; P. M. Sudha, P. S. S. Rao; M. D. Hassan & L. T. Lan, 1998. Managing white spot disease in shrimp, *Infofish International*, 3:30–36). Several species of penaeid shrimps viz. *Penaeus monodon, P. japonicus, P. chinensis, P. indicus, P. merguiensis* and *P. setiferus* have been known to be infected by this virus and the losses reported in China during 1993 was about U.S. $ 1 billion and in Thailand during 1996 was U.S. $ 500 million (Fishing chimes (as reported in Global *Aquaculture Advocate* Vol 2, Issue 2), 1999. What is shrimp white spot disease?, 19: 21–22). The outbreak of the disease was first noticed in India in the Kandaleru creek fed brackishwater farms along the Andhra coast during 1994 (K. M. Shankar & C. V. Mohan, 1994. Kandaleru-fed brackishwater farms near Gudur, A. P., *Fishing Chimes*, September 23–24). Since then it has spread to shrimp farms located along both the coasts and caused heavy mortality and revenue loss to the farmers (C. V. Mohan, 1996. Health management strategy for a rapidly developing shrimp industry: An Indian perspective, In Health Management in Asian Aquaculture. Proceeding of the Regional Expert Consultation on Aquaculture Health Management in Asia and the Pacific, Edited by R. P. Subasinghe, J. R. Arthur & M. Shariff, *Fish Tech Pap* No. 360, FAO, Rome, p. 75–87). The estimated revenue loss in India for the year 1995–96 was about Rs. 250–300 billion (I. Karunasagar & I. Karunasagr, 1999. Shrimp disease prevention methods with special reference to white spot disease. Paper presented in the Workshop on Development of Sustainable Management Practices in Shrimp Farming under World Bank Assisted Shrimp and Fish Culture Project, held at Bhubaneswar, Jul. 30–31, 1999). The causative viral agent has been known by different names in different countries such as haematopoietic necrosis baculovirus (HHNBV), systemic ectodermal and mesodermal baculovirus (SEMBV), penaeid rod-shaped DNA virus (PRDV), white spot baculovirus (WSBV), *Penaeus monodon* non-occluded baculovirusII (PmNOBII), *Penaeus monodon* non-occluded baculovirusIII (PmNOBIII) (C. V. Mohan; P. M. Sudha; K. M. Shankar & A. Hedge, 1997. Vertical transmission of white spot baculovirus in shrimps-A possibility? *Curr. Sci.*, 73: 109–110; I. Karunasagar; S. K. Otta & I. Karunasagar, 1997. Histopathological and bacteriological study of white spot syndrome of *Penaeus monodon* along the west coast of India, *Aquaculture*, 153: 9–13; Y. G. Wang; M. Shariff; P. M. Sudha, P. S. S. Rao; M. D. Hassan & L. T. Lan, 1998. Managing white spot disease in shrimp, *Infofish International*, 3:30–36). However, the etiology of the viral agent known by different names has been well studied and has been confirmed to be a baculovirus and is collectively known as the white spot syndrome virus or WSSV (D. V. Lightner, 1996. Handbook of for diagnosis procedures for diseases of penaeid shrimp, Special Publication of the World Aquaculture Society, Baton Rouge, La., Section 3.11). WSSV has been shown to target various tissues originating from both the mesoderm and ectoderm as evidenced by histopathological studies (C. Wongteerasupaya; J. E. Vickers; S. Sriurairatana; G. L. Nash; A. Akarajamom; V. Boonsaeng; S. Panyim; A. Tassnakajon; B. Withyachumnamkul & T. W. Flegel, 1995. A. non-occluded, systemic baculovirus that occurs in cells of ectodermal and mesodermal origin and causes high mortality in the black tiger prawn *Penaeus monodon*, Dis. Aquat. Org., 21: 69–77) and in situ hybridization ((P. S. Chang; C. F. Lo; Y. C. Wang & G. H. Kou, 1996. Identification of white spot syndrome associated baculovirus (WSBV) target organs in the shrimp *Penaeus monodon* by in situ hybridization, *Dis. Aquat. Org.*, 27: 131–139). These studies were conducted on farm produced shrimps and/or experimentally infected shrimps. In another study, the virus has also been detected in different organs/tissues including the reproductive organs of wild caught brooders of *Penaeus monodon* indicating its vertical transmission (Chu-Fang Lo; Ching-Hui Ho; Chau-Huei Chen; Kuan-Fu Liu; Ya-Lin Chiu; Pie-Yan Yeh; Shao-En Peng; Hui-Chen Hsu; Hwei-Chung Liu; Chen-Fang Chang; Mao-Sen Su; Chung-Hsiung Wang & Guang-Hsiung Kou, 1997. Detection and tissue tropism of white spot syndrome baculovirus (WSBV) in captured brooders of *Penaeus monodon* with a special emphasis on reproductive organs, *Dis. Aquat. Org.*, 30: 53–72).

Some plants have been used to control the severity of certain types of viral diseases. The ethanol extracts of two species of the genus Phyllanthus vis. *P. amarus* and *P. urinaria* homogenised with lobster haemolymph medium and injected into healthy *Penaeus monodon* after mixing with the yellow-head baculovirus (YBV), showed antivirucidal activity at a concentration of 100 μg/ml and 1 mg/ml, respectively against yellowhead baculovirus (YBV) (S. Direkbusarakom; A. Hurunsalee; S. Boonyaratpalin; Y. Danayadol & U. Aekpanithanpong, 1993. Effect of Phyllanthus spp. Against yellow-head baclovirus infection in black tiger shrimp, *Penaeus monodon*, In Diseases in Asian Aquaculture II, Fish Health Section, Edited by M. Shariff, J. R. Arthur & R. P. Subasinghe , Asian Fish. Soc., Manila, p. 81–88). However, these extracts have not been tested on the WSSV.

The ethanol extract of the leaves of Thai traditional medicine against human viral disease viz. *Clinacanthus nutans* Lindua, injected into the tiger shrimp showed inhibition of the yellow-head rhabdovirus (YRV) at a concentration of 1 μg/ml and by oral application at the rate of 1 g/kg of pellet feed (S. Direkbusarakom; L. Ruangpan; Y. Ezura & M. Yoshimizu, 1998. *Fish. Pathol.*, 33: 401–404). This extract has also not been tested on controlling the WSSV.

The Gauva leaf (*Psidium guajava*), was not found to be effective on yellow-head virus infection in tiger shrimp although it was effective in preventing bacterial infection in cat fish (S. Direkbusarakom; A. Herunsalee; M. Yoshimizu; Y. Ezura & T. Kimura, 1997. Efficacy of Guava (*Psidium guajava*) extract against some fish and shrimp pathogenic agents, In Diseases in Asian Aquaculture III. Fish Health Section, Edited by T. W. Flegel & I. H. MacRae, Asian Fisheries Society, Manila, p. 359–363).

It has been reported that the extract of an Indian wild plant, 'Swallow Wort' is useful in combating white spot virus (Anonymous, 1997. Wild plant combats WSV, *Infofish International*, No.2, March/April, 1997). However, no details on the therapeutic dosage and effects have been made available.

There also appeared a report that the extract of the weed *Calotropis gigantea* is able to arrest mortality in white spot infects shrimps (MPEDA, 1996. Herbal treatment for shrimp virus, UNI report in Indian Express, Jul. 18, 1996), but did not mention the dosage and related details.

OBJECTS OF THE PRESENT INVENTION

The main objective of the present invention is to provide a composition useful as prophylactic and therapeutic agent for the management of viral and bacterial diseases in aquatic animals.

Particularly, the objective of the present invention is to provide a composition useful for improving health and reducing mortality rate in tiger shrimp *Penaeus monodon*.

More particularly, the objective of the present invention is to provide a composition for the treatment of white spot disease in the tiger shrimp *Penaeus monodon*.

Another object of the present invention is to provide a process for the preparation of the composition useful as prophylactic and therapeutic agent for the management of viral and bacterial diseases in aquatic animals.

Yet another object of the present invention is to provide a method for reducing the mortality rate in the tiger shrimp *Penaeus monodon*.

Still another object of the present invention is to provide a method for the treatment of white spot disease in the tiger shrimp *Penaeus monodon*.

SUMMARY OF THE INVENTION

The present invention relates to a composition useful as prophylactic and therapeutic agent for the management of viral and bacterial diseases in aquatic animals. The invention also relates to a process for the preparation of the composition and a process for the treatment of the aquatic animals using the said composition.

BRIEF DESCRIPTION OF THE ACCOMPANYING DRAWINGS

The patent or application file contains at least one drawing executed in color. Copies of this patent or patent application publication with color drawings will be provided by the Office upon request and payment of the necessary fee.

In the photographs accompanying the specification,

FIG. 1 represents the clinical signs such as reddening of the cephalothorax, white spots on the inner surface of the carapace and lesion on the body surface of the affected tiger shrimp *Penaeus monodon*.

Figure 2:
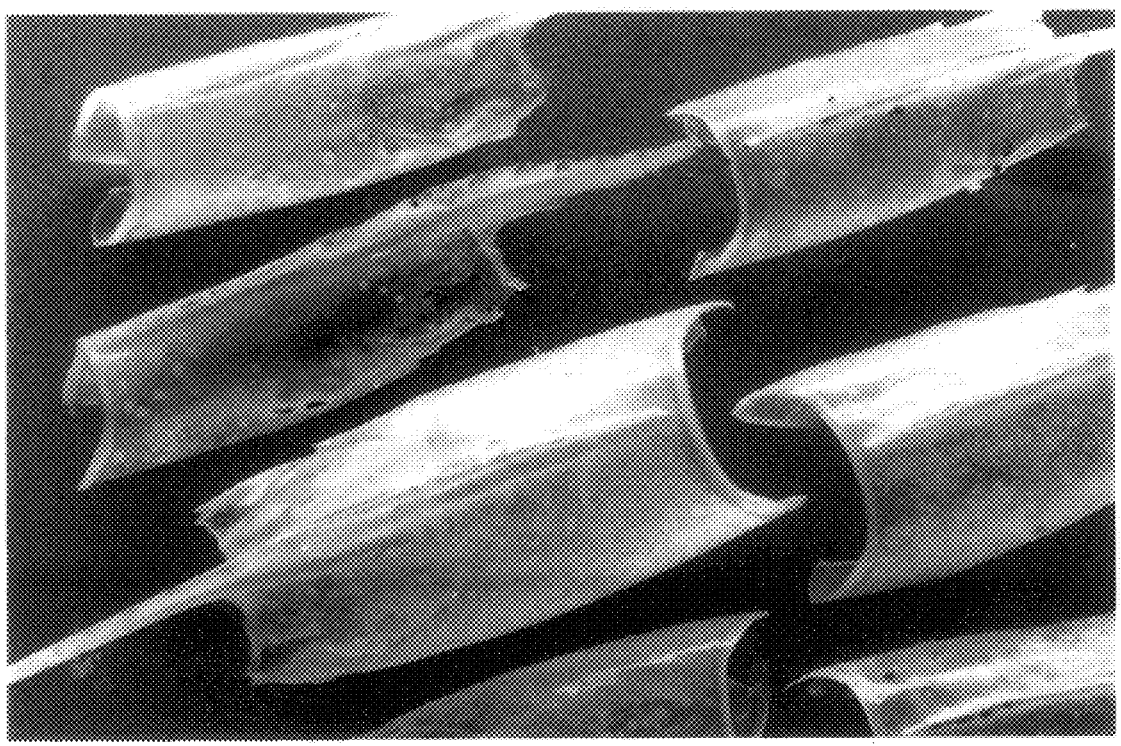

In the accompanying FIG. 2, represents the carapace of the affected tiger shrimps having intense distribution of white spots which is an important clinical sign of whitespot syndrome in shrimps.

Figure 3:
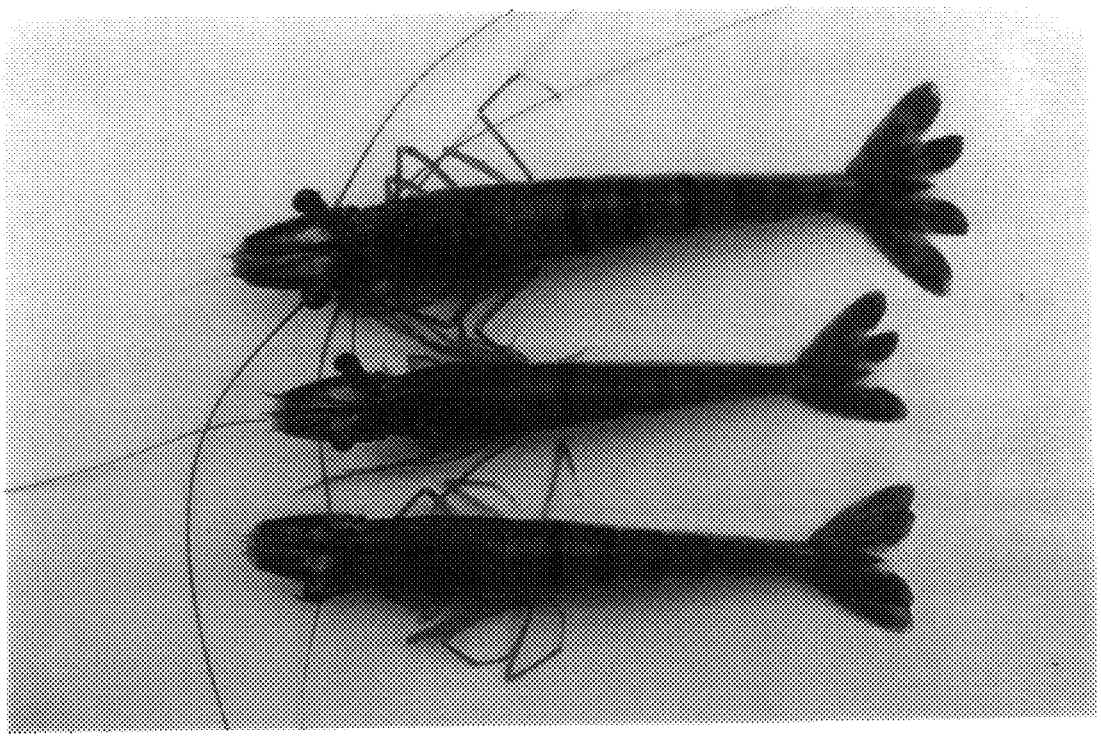

In the accompanying FIG. 3, represents previously affected tiger shrimps regaining normal health and attaining normal pigmentation after exposure to the plant extract.

Figure 4:
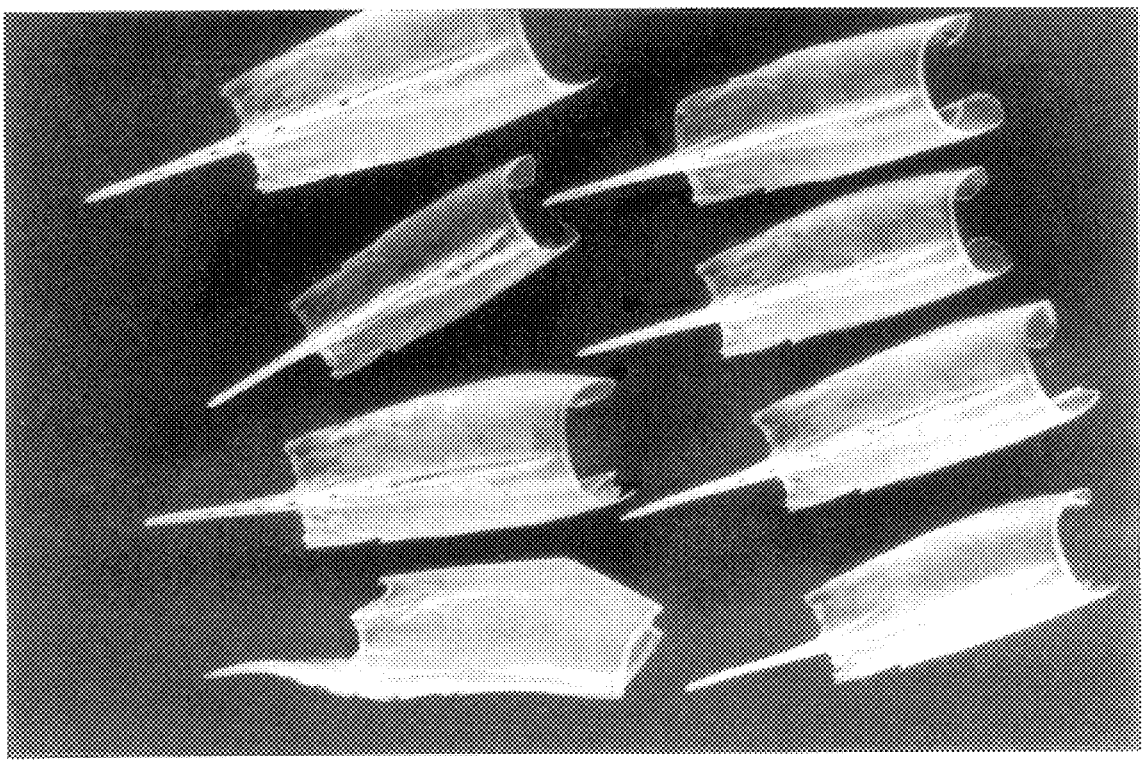

In the accompanying FIG. 4, represents the carapace of previously affected shrimps showing no white spots after exposure to the plant extract.

Figure 5:
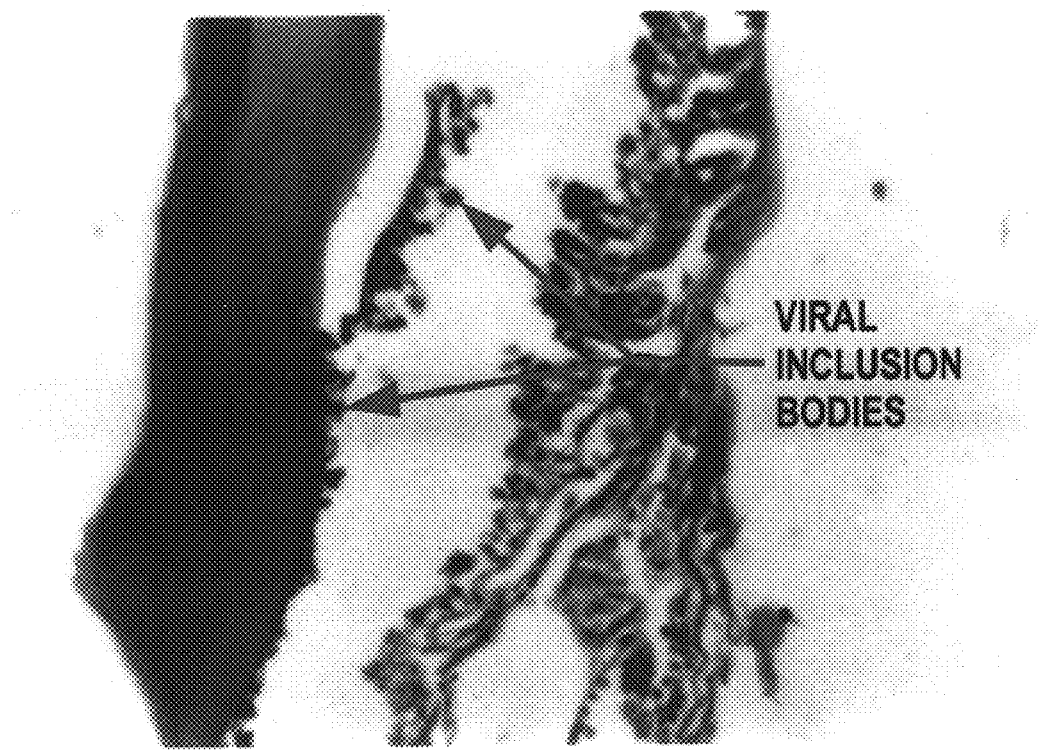

In the accompanying FIG. 5, represents the cuticular epidermis of infected shrimp before exposure to the plant extract. The presence of basophilic intranuclear viral inclusion bodies in the cuticular epidermal cells is a diagnostic feature of WSSV infection.

Figure 6:
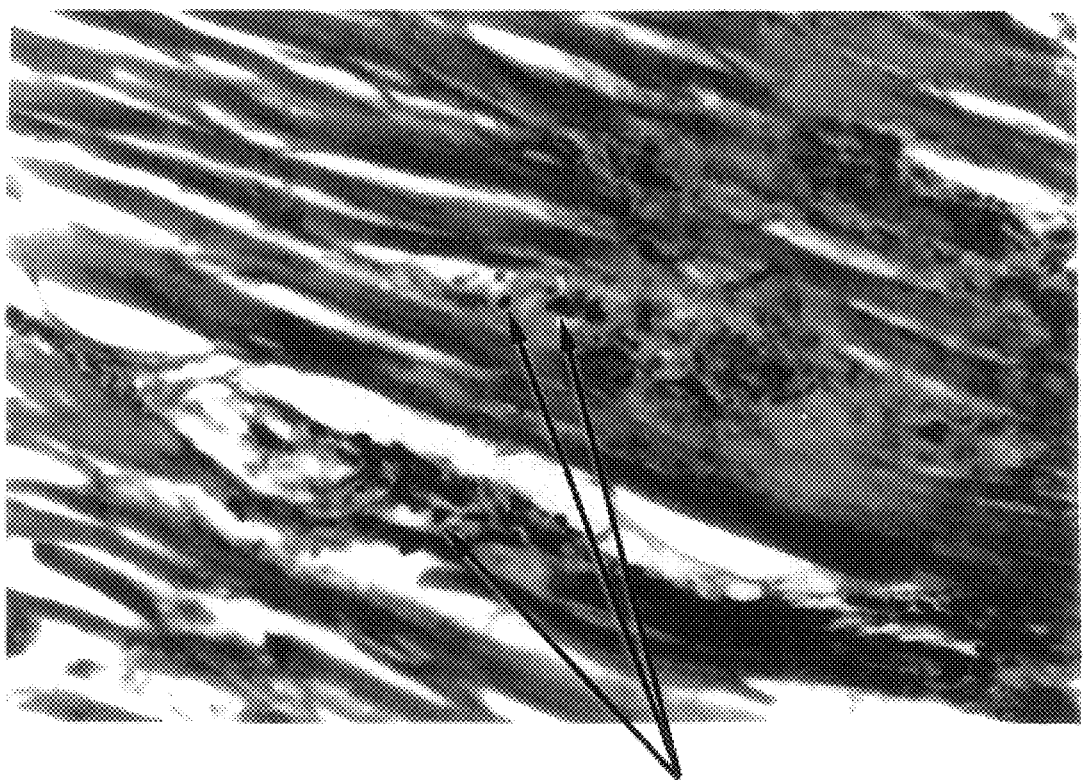

In the accompanying FIG. 6, represents the intramusclular fibrosis in the infected shrimp with presence of viral inclusion bodies in the inflammatory tissue in the muscle before exposure to the plant extract.

Figure 7:
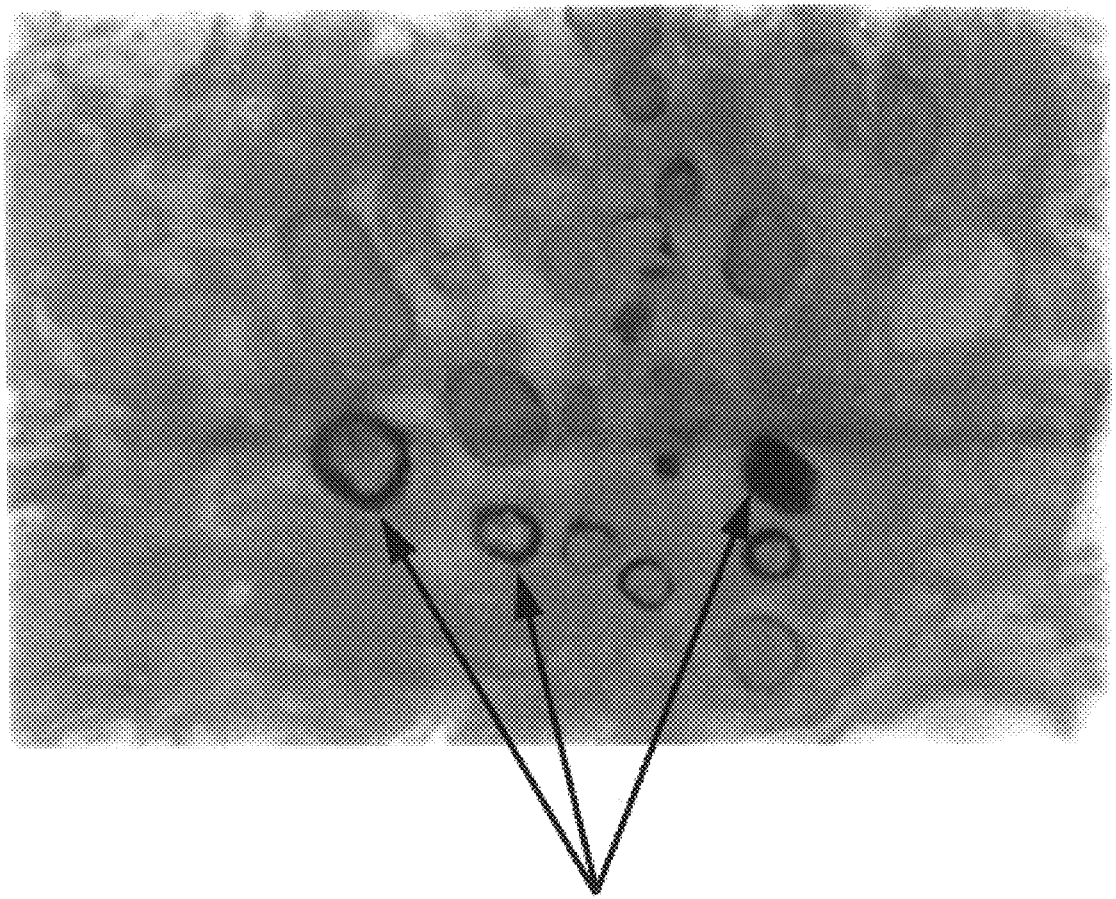

In the accompanying FIG. 7, represents the melanised nodule formation in the hepatopancreas in the infected shrimp before exposure to the plant extract. The melanised nodule is a diagnostic feature of bacterial infection. The pathology in the muscle and hepatopancreas suggests a mixed infection with WSSV and bacteria.

Figure 8:

In the accompanying FIG. 8, represents the cuticle of a previously infected shrimp after exposure to the plant extract, showing no intranuclear viral inclusion bodies in the epidermal cells.

Figure 9:
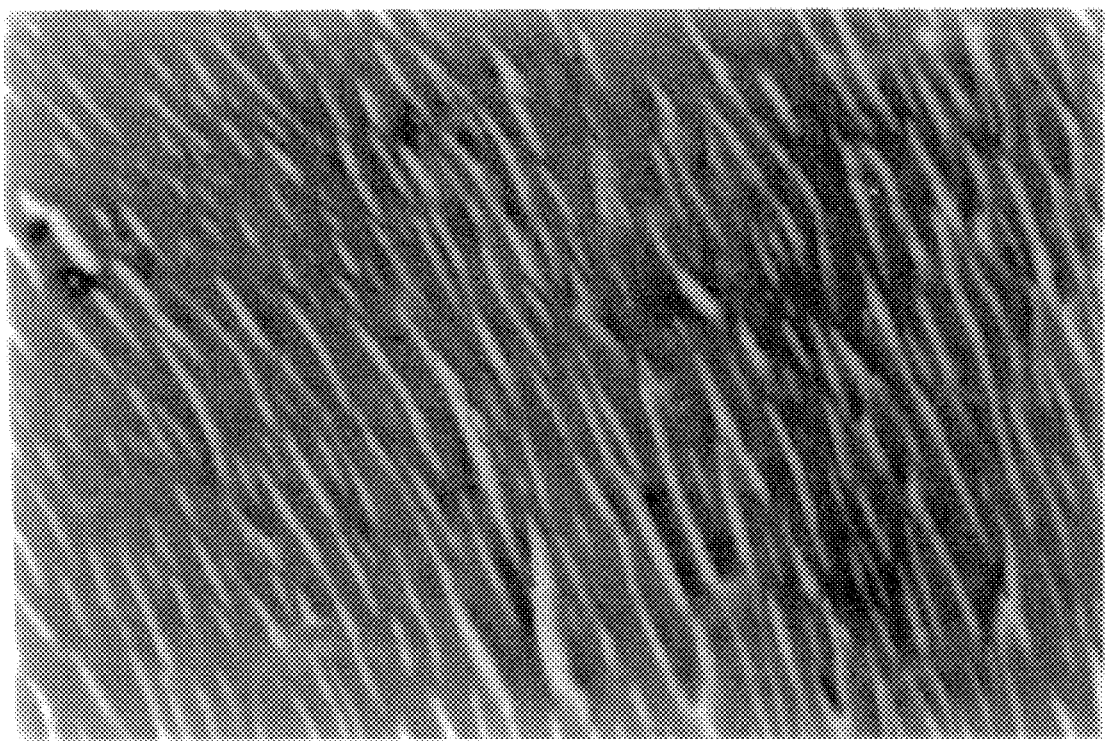

In the accompanying FIG. 9, represents the muscle of a previously infected shrimp after exposure to the plant extract, showing no fibrosis.

Figure 10:
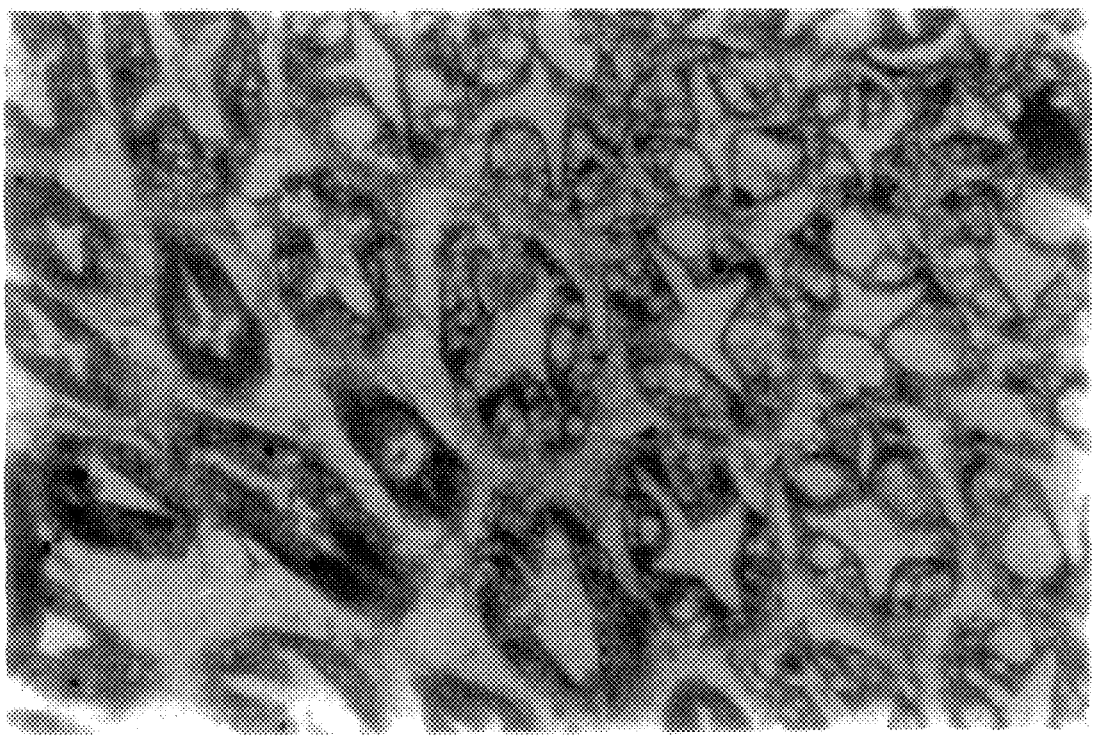

In the accompanying FIG. 10, represents the hepatopancreas of a previously infected shrimp after exposure to the plant extract, showing no melanised nodules.

DETAILED DESCRIPTION OF THE INVENTION

Accordingly the present invention provides a composition useful as prophylactic and/or therapeutic agent for the management of viral and bacterial diseases in aquatic animals, said composition containing effective amount of extract obtained from the plants *Lantena camera, Aegle marmelos, Ocimum sanctum, Mimosa pudica, Cynodon dactylon, Curcuma longa*, and *Allium sativum*, optionally in combination with a pharmaceutically acceptable carrier diluents or excipients.

In an embodiment of the present invention, the extract contains 25 to 40 per cent by Wt. *Lantena camera*, 10 to 20 per cent by Wt. *Aegle marmelos*, 10 to 20 per cent by Wt. *Ocimum sanctum*, 10 to 15 per cent by Wt. *Mimosa pudica*, 5 to 10 per cent by Wt. *Cynodon dactylon*, 5 to 10 per cent by Wt. *Curcuma longa* and 1 to 8 per cent by Wt. *Allium sativum*.

In a preferred embodiment of the present invention, the extract contains 30 to 35 per cent by Wt. *Lantena camera*, 14 to 18 per cent by Wt. *Aegle marmelos*, 15 to 18 per cent by Wt. *Ocimum sanctum*, 11 to 14 per cent by Wt. *Mimosa pudica*, 7 to 8.5 per cent by Wt. *Cynodon dactylon*, 8 to 8.5 per cent by Wt. *Curcuma longa* and 3 to 5 per cent by Wt. *Allium sativum*.

In another embodiment of the-present invention, the extract is selected from aqueous extract, chloroform extract and hexane extract.

In still another embodiment of the present invention, the extract is a ground paste of the following plant parts: 200 g of *Lantena camera*, 100 g of *Aegle marmelos*, 100 g of *Ocimum sanctum*, 75 g of *Mimosapudica*, 50 g of *Cynodon dactylon*, 50 g of *Curcuma longa* and 25 g of *Allium sativum*, which is added with water to make the final volume to 1 liter.

In yet another embodiment of the present invention, the plant parts are selected from tender leaves, branches, stem and roots.

In one more embodiment of the present invention, the carrier is zeolite.

In one another embodiment of the present invention, the ratio of zeolite and the concentrated extract is maintained between 2:1 to 6:1 (w/v).

In one another preferred embodiment of the present invention, the ratio of zeolite and the concentrated extract is maintained at 4:1 (w/v).

In an embodiment of the present invention, the composition is used for the treatment of white spot disease in the tiger shrimp *Penaeus monodon*.

In another embodiment of the present invention, the composition improves the health and reduces the mortality rate in white spot syndrome virus (WSSV) infected tiger shrimp *Penaeus monodon*.

In still another embodiment of the present invention, 5 to 15 ppm of the composition arrest the advancement of white spot syndrome virus (WSSV) infection both clinically and behaviorally within 2 to 5 days in the tiger shrimp *Penaeus monodon*.

In yet another embodiment of the present invention, 5 to 15 ppm of the composition reduces the mortality rate of WSSV infected tiger shrimp *Penaeus monodon* by 5 to 20%.

In one more embodiment of the present invention, 5 to 15 ppm of the composition induces moulting within 12 to 17 days in WSSV infected tiger shrimp *Penaeus monodon*.

The present invention also provides a process for preparing the composition useful as prophylactic and/or therapeutic agent for the management of viral and bacterial diseases in aquatic animals, said process comprising: obtaining an extract from the plant parts of *Lantena camera, Aegle marmelos, Ocimum sanctum, Mimosa pudica, Cynodon dactylon, Curcuma longa*, and *Allium sativum*, and optionally adding a pharmaceutically acceptable carrier diluents or excipients to the extract.

In a preferred embodiment of the present invention, the process for obtaining a composition comprises of (i) obtaining 200 g of *Lantena camera*, 100 g of *Aegle marmelos*, 100 g of *Ocimum sanctum*, 75 g of *Mimosa pudica*, 50 g of *Cynodon dactylon*, 50 g of *Curcuma longa* and 25 g of *Allium sativum* plant parts; (ii) mixing and grinding them to fine paste; (iii) making the final volume to 1 liter by adding water and (iv) adding optionally a carrier to the extract.

In an embodiment of the present invention, the plant parts are selected from tender leaves, stem, branches and roots.

In another preferred embodiment of the present invention, the plant parts are washed before subjecting them to grinding.

In another embodiment of the present invention, the carrier is zeolite.

In still another embodiment of the present invention, the ratio of the carrier to the extract is maintained between 2:1 to 6:1 (w/v).

In still another preferred embodiment of the present invention, the ratio of the carrier to the extract is maintained at 4:1 (w/v).

The invention further provides a method for treating white spot disease in aquatic animals, said process comprising introducing an effective amount of a composition containing extract obtained from the plants *Lantena camera, Aegle marmelos, Ocimum sanctum, Mimosa pudica, Cynodon dactylon, Curcuma longa*, and *Allium sativum*, optionally in combination with a pharmaceutically acceptable carrier diluents or excipients into the habitat of the aquatic animals.

In an embodiment of the present invention, the extract contains 25 to 40 per cent by Wt. *Lantena camera*, 10 to 20 per cent by Wt. *Aegle marmelos*, 10 to 20 per cent by Wt. *Ocimum sanctum*, 10 to 15 per cent by Wt. *Mimosa pudica*, 5 to 10 per cent by Wt. *Cynodon dactylon*, 5 to 10 per cent by Wt. *Curcuma longa* and 1 to 8 per cent by Wt. *Allium sativum*.

In a preferred embodiment of the present invention, the extract contains 30 to 35 per cent by Wt. *Lantena camera*, 14 to 18 per cent by Wt. *Aegle marmelos*, 15 to 18 per cent by Wt. *Ocimum sanctum*, 11 to 14 per cent by Wt. *Mimosa pudica*, 7 to 8.5 per cent by Wt. *Cynodon dactylon*, 8 to 8.5 per cent by Wt. *Curcuma longa* and 3 to 5 per cent by Wt. *Allium sativum*.

In another embodiment of the present invention, the carrier is zeolite.

In still another embodiment of the present invention, the ratio of the carrier to the extract is maintained between 2:1 to 6:1 (w/v).

In still another preferred embodiment of the present invention, the ratio of the carrier to the extract is maintained at 4:1 (w/v).

In yet another embodiment of the present invention, the white spot syndrome virus (WSSV) infected animals receives 5 to 15 ppm of the said composition or the extract.

In one more embodiment of the present invention, the white spot syndrome virus (WSSV) infected animals showed improvement in clinical and behavior sign in 2 to 5 days.

In one another embodiment of the present invention, the white spot syndrome virus (WSSV) infected animals regained the original pigmentation, active swimming, intense feeding, normal feces production, disappearance of white spots, swelling became normal in 10 to 17 days.

In an embodiment of the present invention, the moulting occurred between 12 and $17^{th}$ day in the white spot syndrome virus (WSSV) infected animals.

In another embodiment of the present invention, the mortality rate of the white spot syndrome virus (WSSV) infected animals is reduced by 5 to 20 per cent.

In still another embodiment of the present invention, a composition containing effective amount of extract obtained from the plants *Lantena camera, Aegle marmelos, Ocimum sanctum, Mimosa pudica, Cynodon dactylon, Curcuma longa*, and *Allium sativum*, optionally in combination with a pharmaceutically acceptable carrier diluents or excipients is used as prophylactic and/or therapeutic agent for the management of viral and/or bacterial diseases in aquatic animals by introducing the said composition into the habitat of the aquatic animals.

In yet another embodiment of the present invention, the extract contains 25 to 40 per cent by Wt. *Lantena camera*, 10 to 20 per cent by Wt. *Aegle marmelos*, 10 to 20 per cent by Wt. *Ocimum sanctum*, 10 to 15 per cent by Wt. *Mimosa pudica*, 5 to 10 per cent by Wt. *Cynodon dactylon*, 5 to 10 per cent by Wt. *Curcuma longa* and 1 to 8 per cent by Wt. *Allium sativum* is used as prophylactic and/or therapeutic agent for the management of viral and/or bacterial diseases in aquatic animals by introducing the said composition into the habitat of the aquatic animals.

In one more embodiment of the present invention, the extract contains 30 to 35 per cent by Wt. *Lantena camera*, 14 to 18 by Wt. per cent *Aegle marmelos*, 15 to 18 per cent by Wt. *Ocimum sanctum*, 11 to 14 per cent by Wt. *Mimosa pudica*, 7 to 8.5 per cent by Wt. *Cynodon dactylon*, 8 to 8.5 per cent by Wt. *Curcuma longa* and 3 to 5 per cent by Wt. *Allium sativum* is used as prophylactic and/or therapeutic agent for the management of viral and/or bacterial diseases in aquatic animals by introducing the said composition into the habitat of the aquatic animals.

In one another embodiment of the present invention, the composition or the extract mixture is used for treating white spot disease in the tiger shrimp *Penaeus monodon*.

In one another embodiment of the present invention, the composition or the extract mixture is used for improving the health and reducing the mortality rate in white spot syndrome virus (WSSV) infected tiger shrimp *Penaeus monodon*.

In an embodiment of the present invention, the composition or the extract mixture is used for arresting the advancement of white spot syndrome virus (WSSV) infection in tiger shrimp *Penaeus monodon*.

In another embodiment of the present invention, the composition or the extract mixture is used for reducing the mortality rate of white spot syndrome virus (WSSV) infected tiger shrimp *Penaeus monodon* by 5 to 20%.

In still another embodiment of the present invention, the composition or the extract mixture is used for inducing moulding in white spot syndrome virus (WSSV) infected tiger shrimp *Penaeus monodon*.

In yet another embodiment of the present invention, 5 to 15 ppm of the composition or the extract mixture is used for treating white spot disease in the tiger shrimp *Penaeus monodon*.

In one more embodiment of the present invention, the composition or the extract mixture is used to improve clinical and behavior signs in white spot syndrome virus (WSSV) infected tiger shrimp *Penaeus monodon* in 2 to 5 days.

The invention is further explained with the help of the following examples and should not be construed to limit the scope of the invention.

EXAMPLES

Example 1

Tender leaves of *Lantena camera* (200 g), *Aegle marmelos* (100 g) *Ocimum sanctum* (100 g), *Mimosa pudica* (75 g), *Cynodon dactylon* (50 g), *Curcuma longa* (50 g) and *Allium sativum* (25 g) were used to prepare the aqueous extract. Freshly collected leaves of the above mentioned plants in the quantities shown within parentheses were mixed and washed thoroughly with distilled water. They were ground to a fine paste in a warning blender using required volume of distilled water. Final volume of the extract was made to 1 liter by adding required volume of distilled water and mixed well. The extract was passed through a bolting silk of 0.5 mm mesh to remove large particles. The example illustrates the method for the preparation of the stock aqueous extract of the leaves.

Example 2

White spot syndrome virus (WSSV) infected shrimps were collected from a shrimp farm located in South Goa. *Penaeus monodon* (tiger shrimp) weighing on an average, 20 g was chosen for testing. Infection on the shrimps was decided based on clinical as well as behavioural sign, such as white spots on the inner surface of carapace, red colouration on the cephalothorax and some appendages, loose cuticle, lesions on the body, swollen gills, lack of feeding, sluggish movements, tendency to swim inactively along the periphery of the ponds, etc. Shrimps were caught using a cast net and infected ones were carefully removed to large plastic buckets containing the pond water. They were brought to the laboratory under aeration. In the laboratory the specimens were transferred carefully into a rectangular fibreglass tanks (1 $m^3$ capacity) containing sand filtered continuously aerated seawater of salinity 30 ppt. This examples illustrates the collection and acclimatisation to laboratory condition. of WSSV infected shrimps.

Example 3

Three rectangular fibreglass tanks (capacity 1 $m^3$), each containing 500 liters of sand filtered seawater of salinity 30 ppt and pH 7.8, having continuous aeration was kept ready. Twenty infected shrimps were transferred with care into each tank. The shrimps were fed a combination of fresh squids and mussels at the rate of 8% of the total body weight in the evening after removing excess feed and moults. Required volume of the stock extract was added in one tank to make 5 ppm concentration. The concentration of extract in the second tank was made to 15 ppm. The third tank was kept as the control without adding the extract. Fifty percent of the water was exchanged every day including the control tank and concentration of extract in the tanks were adjusted accordingly.

Example 4

Daily records of the clinical sign and behaviour aspects of the shrimps were monitored to test the efficacy of the extract in controlling the infection and improving the health of the shrimps. The observations were made for 25 days (Tables 1 & 2). In control, the clinical sign remained as they were with out any improvement. No moulting occurred during this period and mortality occurred frequently. The shrimps exposed to 5 ppm of the extract, showed improvement in clinical signs and behaviour within 5 days and regained the original pigmentation, active swimming, intense feeding, normal feces production, etc. within 17 days. Moulting occurred within 17 days and mortality did not exceed 20% at the end of the experimental duration. This example illustrates the effect of the extract at 5 ppm concentration in controlling the infection in the test animals, improving the overall health, reducing mortality and inducing moulting.

TABLE 1

Clinical sign in infected *Penaeus monodon* and those exposed at 5 and 15 ppm concentration of the plant extract

| Shrimps | White spots | Colour/pig-mentation | Lesions | Swelling |
|---|---|---|---|---|
| Infected (Control) | Intense on inner surface of carapce; scattered on body | Reddening of cephalo-thorax and some appeandages | Present on body | Gills and some appendages |
| Exposed at 5 ppm conc. after 5 days | Reduced intensity; color of spots not prominent | Red colour intensity reduced; pigmentation improved | Healing started | Considerably reduced |
| Exposed at 5 ppm conc. after 17 days | Spots disappeared | Normal colour regained; No reddening visible | Mostly healed | Completely cured |
| Exposed at 15 ppm conc. After 2 days | Reduced intensity; spots not prominent | Red colour intensity reduced; pigmentation improved | Healing started | Considerably reduced |
| Exposed at 15 ppm conc. After 10 days | Spots disappeared | Normal colour regained; No reddening visible | Completely healed | Completely cured |

TABLE 2

Behavioural sign in infected *Penaeus monodon* and those exposed at 5 and 15 ppm concentration of the plant extract

| Shrimps | Feeding | Feces | Moulting | Swimming | Mortality |
|---|---|---|---|---|---|
| Infected (Control) | Poor feeding; empty gut | Yellowish, mostly empty and broken strands | No moulting | Sluggish | Frequent |
| Exposed at 5 ppm conc. after 5 days | Feeding improved; half to near full guts | Brownish, long and almost full strands | No moulting | Less active | <20% |
| Exposed at 5 ppm conc. After 17 days | Actively feeding; mostly full gut | Dark, long and full strands | Within 17 days | Very active | <20% |
| Exposed at 15 ppm conc. after 2 days | Feeding improves; half to near full guts | Yellowish, mostly empty and broken strands | No moulting | Less active | <5% |
| Exposed at 15 ppm conc. after 10 days | Actively feeding; mostly full gut | Dark, long and full strands | Within 12 days | Very active | <5% |

Example 5

At 15 ppm concentration of the extract (Tables 1 & 2), the shrimps showed immediate improvement (within 2 days) in clinical sign and behavioural aspects. Within 10 days, the white spots on the carapace disappeared, pigmentation became normal, swelling on appendages and gills was negligible, lesions were mostly healed, feeding and feces production became normal, swimming became active and moulting occurred within 12 days. Mortality was observed to be negligible (<5%) during the period of the experiment. This example illustrates that the extract at 15 ppm concentration can reduce the severity of the infection quickly, bring down the mortality rate, improve health in a shorter period and induce moulting early as compared to 5 ppm concentration.

Example 6

Samples for histopathology were routinely fixed in 10% formalin. Fixed samples were dissected and cassetted. Cassetted samples were processed using an automatic tissue processor, embedded using a wax embedding centre. The blocks were trimmed and 5 $\mu$m sections cut, fixed, stained and observed according to the standard procedure (D. V. Lightner, 1996. A handbookof pathology and diagnostic procedures for diseases of penaeid shrimp. Special Publication of the World Aquaculture Society, Baton Rouge, La., Section 3.11). This example illustrates the procedure followed for preparation of different tissues for histopathological studies.

Example 7

Control animals which were not exposed to the extract showed consistent pathological features such as basophilic intranuclear inclusions in the cuticular epidermal cells which is a diagnostic feature for WSSV infection. The animals showed fibrosis in the muscle tissue and melanised nodule formation in the hepatopancreas which are diagnostic for enteric and systemic bacteriaemia. The affected animals were having mixed viral and bacterial infection. This example illustrates the histopathology of the different tissues of the infected shrimp.

Example 8

The histopathology of the affected animals after exposure to the plant extract showed no evidence of any intramuscular inclusion bodies in the cuticular epidermis. There was also no evidence of any fibrosis in the muscle or melanised nodules in the hepatopancreas. Histologically, after exposure to the plant extract, the shrimps appeared to be normal and there was no evidence of any pathology or infection. This examples illustrates the histopathological evidences of different tissues after exposure to the plant extract.

Advantages of the Leaf Extract

This is for the first time that extract of selected plants were found to be effective in controlling WSSV infection in farm produced shrimps.

Growth in shrimps (in crustaceans generally) is effected through an important physiological process known as moulting (shedding of exoskeleton). In WSSV infected shrimps the exoskeleton becomes loose and soft and moulting is either delayed or does not take place leading to heavy mortality. It was found that the extract was able to induce moulting in the infected shrimps.

Moulting makes the new exoskeleton hard, regains pigmentation and fissures and other damages seen on the body start healing.

Mortality rate comes down considerably, shrimp regain normal health and becomes active.

The extract may have application as a therapeutantic and/or prophylactic agent in viral disease management in aquaculture practices.

What is claimed is:

1. A composition useful as prophylactic and/or therapeutic agent for the management of white spot disease in aquatic animals, said composition containing effective amounts of extracts obtained from the plants *Lantena camera, Aegle marmelos, Ocimum sanctum, Mimosa pudica, Cynodon dactylon, Curcuma longa*, and *Allium sativum*, optionally in combination with a pharmaceutically acceptable carrier, diluents or excipients.

2. A composition as claimed in claim 1, wherein the extract contains 25 to 40 per cent by Wt. *Lantena camera*, 10 to 20 per cent by Wt. *Aegle marmelos*, 10 to 20 per cent by Wt. *Ocimum sanctum*, 10 to 15 per cent by Wt. *Mimosa pudica*, 5 to 10 per cent by Wt. *Cynodon dactylon*, 5 to 10 per cent by Wt. *Curcuma longa* and 1 to 8 per cent by Wt. *Allium sativum*.

3. A composition as claimed in claim 1, wherein the extract contains 30 to 35 per cent by Wt. *Lantena camera*, 14 to 18 per cent by Wt. *Aegle marmelos*, 15 to 18 per cent by Wt. *Ocimum sanctum*, 11 to 14 per cent by Wt. *Mimosa pudica*, 7 to 8.5 per cent by Wt. *Cynodon dactylon*, 8 to 8.5 per cent by Wt. *Curcuma longa* and 3 to 5 per cent by Wt. *Allium sativum*.

4. A composition as claimed in claim 1, wherein the extract is selected from aqueous extract, chloroform extract and hexane extract.

5. A composition as claimed in claim 1, wherein the extract is a ground paste of the following plant parts: 200 g of *Lantena camera*, 100 g of *Aegle marmelos*, 100 g of *Ocimum sanctum*, 75 g of *Mimosa pudica*, 50 g of Cynodon dactylon, 50 g of *Curcuma longa* and 25 g of *Allium sativum*, which is added with water to make the final volume as 1 liter.

6. A composition as claimed in claim 1, wherein the plant parts are selected from tender leaves, branches, stem and roots.

7. A composition as claimed in claim 1, wherein the carrier is zeolite.

8. A composition as claimed in claim 1, wherein the ratio of zeolite and the concentrated extract is maintained between 2:1 to 6:1 (w/v).

9. A composition as claimed in claim 1, wherein the ratio of zeolite and the concentrated extract is maintained at 4:1 (w/v).

10. A composition as claimed in claim 1, wherein the composition is used for the treatment of white spot disease in the tiger shrimp *Penaeus monodon*.

11. A composition as claimed in claim 1, wherein the composition improves the health and reduces the mortality rate in white spot syndrome virus (WSSV) infected tiger shrimp *Penaeus monodon*.

12. A composition as claimed in claim 1, wherein 5 to 15 ppm of the composition arrest the advancement of white spot syndrome virus (WSSV) infection both clinically and behaviorally within 2 to 5 days in the tiger shrimp *Penaeus monodon*.

13. A composition as claimed in claim 1, wherein 5 to 15 ppm of the composition reduces the mortality rate of WSSV infected tiger shrimp *Penaeus monodon* by 5 to 20%.

14. A composition as claimed in claim 1, wherein 5 to 15 ppm of the composition induces moulting within 12 to 17 days in WSSV infected tiger shrimp *Penaeus monodon*.

15. A process for preparing a composition useful as prophylactic and/or therapeutic agent for the management of white spot disease in aquatic animals, said process comprising: obtaining extracts from the plants *Lantena camera, Aegle marmelos, Ocimum sanctum, Mimosa pudica, Cynodon dactylon, Curcuma longa*, and *Allium sativum*, combining effective amounts of said extracts and optionally adding pharmaceutically acceptable carriers, diluents or excipients to the extracts.

16. A process as claimed in claim 15, wherein the extracts are obtained by grinding 200 g of *Lantena camera*, 100 g of *Aegle marmelos*, 100 g of *Ocimum sanctum*, 75 g of *Mimosa pudica*, 50 g of *Cynodon dactylon*, 50 g of *Curcuma longa* and 25 g of *Allium sativum* to a fine paste; and (ii) adding water to a final volume of 1 liter.

17. A process as claimed in claim 15, wherein the plant parts are selected from tender leaves, stem, branches and roots.

18. A process as claimed in claim 15, wherein the plant parts are washed before subjecting them to grinding.

19. A process as claimed in claim 15, wherein the carrier is zeolite.

20. A process as claimed in claim 15, wherein the ratio of the carrier to the extract is maintained between 2:1 to 6:1 (w/v).

21. A process as claimed in claim 15, wherein the ratio of the carrier to the extract is maintained at 4:1 (w/v).

22. A method for treating white spot disease in aquatic animals, said method comprising introducing of a composition containing effective amounts of extracts obtained from the plants *Lantena camera, Aegle marmelos, Ocimum sanctum, Mimosa pudica, Cynodon dactylon, Curcuma longa*, and *Allium sativum*, optionally in combination with a pharmaceutically acceptable carrier diluents or excipients into the habitat of the aquatic animals.

23. A method as claimed in claim 22, wherein the extract contains 25 to 40 per cent by Wt. *Lantena camera*, 10 to 20 per cent by Wt. *Aegle marmelos*, 10 to 20 per cent by Wt. *Ocimum sanctum*, 10 to 15 per cent by Wt. *Mimosa pudica*, 5 to 10 per cent by Wt. *Cynodon dactylon*, 5 to 10 per cent by Wt. *Curcuma longa* and 1 to 8 per cent by Wt. *Allium sativum*.

24. A method as claimed in claim 22, wherein the extract contains 30 to 35 per cent by Wt. *Lantena camera*, 14 to 18 per cent by Wt. *Aegle marmelos*, 15 to 18 per cent by Wt. *Ocimum sanctum*, 11 to 14 per cent by Wt. *Mimosa pudica*, 7 to 8.5 per cent by Wt. *Cynodon dactylon*, 8 to 8.5 per cent by Wt. Curcuma longa and 3 to 5 per cent by Wt. *Allium sativum*.

25. A method as claimed in claim 22, wherein the carrier is zeolite.

26. A method as claimed in claim 22, wherein the ratio of the carrier to the extract is maintained between 2:1 to 6:1 (w/v).

27. A method as claimed in claim 22, wherein the ratio of the carrier to the extract is maintained at 4:1 (w/v).

28. A method as claimed in claim 22, wherein the white spot syndrome virus (WSSV) infected animals receives 5 to 15 ppm of the said composition or the extract.

29. A method as claimed in claim 22, wherein the white spot syndrome virus (WSSV) infected animals showed improvement in clinical and behavior sign in 2 to 5 days.

30. A method as claimed in claim 22, wherein the white spot syndrome virus (WSSV) infected animals regained the original pigmentation, active swimming, intense feeding, normal feces production, disappearance of white spots, swelling became normal in 10 to 17 days.

31. A method as claimed in claim 22, wherein the moulting occurred between 12 and $17^{th}$ day in the white spot syndrome virus (WSSV) infected animals.

32. A method as claimed in claim 22, wherein the mortality rate of the white spot syndrome virus (WSSV) infected animals is reduced by 5 to 20 per cent.

* * * * *